United States Patent
Shu (10) Patent No.: US 11,205,961 B2
(45) Date of Patent: Dec. 21, 2021

(54) HYSTERETIC BOOST CONVERTER WITH INDUCTOR PEAK CURRENT GEAR-SHIFTING

(71) Applicant: Texas Instruments Incorporated, Dallas, TX (US)

(72) Inventor: Keliu Shu, Frisco, TX (US)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 322 days.

(21) Appl. No.: 16/384,041

(22) Filed: Apr. 15, 2019

(65) Prior Publication Data

US 2020/0328679 A1    Oct. 15, 2020

(51) Int. Cl.
| | | |
|---|---|---|
| *H02M 1/08* | (2006.01) | |
| *H02M 3/157* | (2006.01) | |
| *G01N 33/00* | (2006.01) | |
| *G08B 17/11* | (2006.01) | |

(52) U.S. Cl.
CPC .......... *H02M 3/157* (2013.01); *G01N 33/004* (2013.01); *G01N 33/0063* (2013.01); *H02M 1/08* (2013.01); *G08B 17/11* (2013.01)

(58) Field of Classification Search
CPC ... G01N 33/004; G01N 33/0063; H02M 1/08; H02M 3/157
USPC ....... 73/31.05; 323/271, 282, 283, 284, 285; 327/108, 109, 110
See application file for complete search history.

(56) References Cited

U.S. PATENT DOCUMENTS

| | | | | |
|---|---|---|---|---|
| 2006/0250121 A1* | 11/2006 | Tzeng | ............. | H03F 3/2171 323/288 |
| 2007/0210772 A1* | 9/2007 | Sawtell | ............. | H02M 3/156 323/282 |
| 2009/0160422 A1* | 6/2009 | Isobe | ............. | H02M 3/156 323/349 |
| 2011/0089917 A1* | 4/2011 | Chen | ............. | H02M 3/1584 323/282 |
| 2015/0077242 A1 | 3/2015 | Simoncic | | |
| 2017/0040895 A1* | 2/2017 | May | ............. | G01R 19/165 |
| 2019/0089245 A1* | 3/2019 | King | ............. | G05F 1/46 |

FOREIGN PATENT DOCUMENTS

| | | |
|---|---|---|
| GB | 2559630 A | 8/2018 |
| TW | 201030686 A | 8/2010 |

OTHER PUBLICATIONS

International Search Report dated Jul. 9, 2020.

* cited by examiner

*Primary Examiner* — William Hernandez
(74) *Attorney, Agent, or Firm* — Ray A. King; Charles A. Brill; Frank D. Cimino (57) ABSTRACT

An electronic device has a DC/DC boost converter that includes a power NFET. The power NFET is coupled between a first pin, which can be coupled to a battery through an inductor, and a second pin that can be coupled to a ground plane. A switch-node is coupled to a third pin, which can be coupled to a diode to provide a boosted output voltage. A gate driver can receive a FET-on signal and drive a gate of the power NFET. A digital logic circuit provides the FET-on signal and includes an Ipeak gear-shifting circuit that dynamically changes the value of a peak inductor current responsive to one or more determinations that are related to one of the boosted output voltage and a switching frequency of the DC/DC boost converter.

17 Claims, 8 Drawing Sheets

HYSTERETIC BOOST CONVERTER WITH INDUCTOR PEAK CURRENT GEAR-SHIFTING

FIELD OF THE DISCLOSURE

Disclosed embodiments relate generally to the field of boost converters. More particularly, and not by way of any limitation, the present disclosure is directed to a hysteretic boost converter with inductor peak current (Ipeak) gear-shifting.

BACKGROUND

During operation of a DC/DC boost converter, the gate voltages and logic to control the power transistor are provided using a feedback loop of the boosted output voltage. When a DC/DC boost converter has a large inductor peak current, the low-side power field effect transistor (FET) needs to receive a gate voltage well above the threshold voltage in order to pass the desired peak inductor current; if a high gate voltage on the low-side power FET is not always possible, the size of the low-side power FET can be increased to accommodate the desired large Ipeak value. However, when the power supply is a low-voltage battery, increasing the size of the power FET may be undesirable due to increased die cost, chip form-factor, and decreased battery lifetime. These conflicting needs are especially present when the boosted output voltage is low, e.g., during start up, especially when the battery voltage drops.

A further issue can arise during operation when the load current drops. With a lighter load, the boost converter doesn't need to work as hard, so that the switching frequency may drop into the audio band and cause interference. A dummy load can be added to maintain the switching frequency at a frequency above the audio band, although this traditional approach significantly reduces the boost converter's efficiency.

SUMMARY

Disclosed embodiments provide two gear-shifting methods that dynamically change the value of the inductor peak current during operation of the boost converter. During startup when the gate voltage is low, the inductor peak current is initially set to a low value. Once the gate voltage increases to the desired operating range, the inductor peak current is dynamically shifted to a target peak value that can be determined, e.g., by register input.

Gear-shifting can also be performed dynamically to lower the value of the inductor peak current in a stepwise fashion when the load current decreases to a point that the switching frequency may drop into the audio band. By lowering the value of the inductor peak current, each cycle of the DC/DC boost converter provides a smaller boost to the output voltage and requires in turn that the switching frequency increase in order to maintain a given output voltage. When the load current rises again, the inductor peak current can be raised in a stepwise fashion to meet the changing needs. The inductor peak current can be lowered in a relatively slow stepwise fashion and raised in a faster stepwise fashion to prevent a drastic drop in the output voltage. Rather than monitoring the switching frequency directly, gear-shifting can be performed responsive to shifts in related indicators, e.g., the idle-state time, which is a component of the cycle time, the cycle time being the inverse of the switching frequency.

In one aspect, an embodiment of an electronic device comprising a DC/DC boost converter is disclosed. The DC/DC boost converter includes a power N-type field effect transistor NFET coupled between a first pin for coupling to a battery voltage through an inductor and a second pin for coupling to a ground plane, a switch-node between the first pin and the power NFET being coupled to third pin for coupling to a diode to provide a boosted output voltage; a gate driver coupled to receive a FET-on signal and to drive a gate of the power NFET; and a digital logic circuit coupled to provide the FET-on signal, the digital logic circuit comprising an Ipeak gear-shifting circuit that is coupled to dynamically change the value of a peak inductor current responsive to one or more determinations related to one of the boosted output voltage and a switching frequency of the DC/DC boost converter.

In another aspect, a method of operating a DC/DC voltage converter is disclosed. The method includes receiving a target peak value for a peak inductor current; and dynamically changing the value of the peak inductor current responsive to one or more determinations related to one of the boosted output voltage and a switching frequency of the DC/DC boost converter.

BRIEF DESCRIPTION OF THE DRAWINGS

Embodiments of the present disclosure are illustrated by way of example, and not by way of limitation, in the figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effect such feature, structure, or characteristic in connection with other embodiments whether or not explicitly described. As used herein, the term "couple" or "couples" is intended to mean either an indirect or direct electrical connection unless qualified as in "communicably coupled" which may include wireless connections. Thus, if a first device couples to a second device, that connection may be through a direct electrical connection, or through an indirect electrical connection via other devices and connections.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing figures in which:

DETAILED DESCRIPTION OF THE DRAWINGS

Specific embodiments of the invention will now be described in detail with reference to the accompanying figures. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Figure 1A:
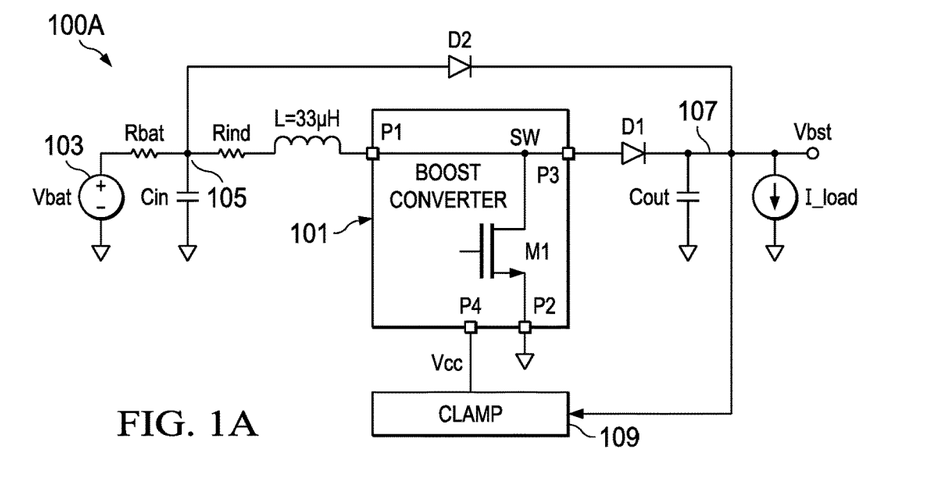
FIG. 1A depicts an example of a DC/DC boost converter in which the disclosed method of operation can be incorporated according to an embodiment of the disclosure.

FIG. 1A depicts an example of a DC/DC boost converter 100A in which the disclosed inductor peak current gear-shifting can be implemented according to an embodiment of the disclosure. A DC/DC boost converter chip 101 includes a low-side power FET M1, which is an N-type power FET, and four pins: first pin P1, second pin P2, third pin P3 and fourth pin P4. Within DC/DC boost converter chip 101, switch node SW lies between the first pin P1 and the third pin P3 and the low-side power FET M1 is coupled between the switch node SW and the second pin P2. An inductor L is coupled between the first pin P1 and a power supply, which in FIG. 1A is a battery 103. An input capacitor Cin has a first terminal coupled to a first node 105 that lies between the battery 103 and inductor L and a second terminal coupled to the lower rail, which can be a ground plane. The battery 103 has a battery voltage Vbat and a battery resistance Rbat; inductor L has an inductor resistance Rind.

The third pin P3 is coupled to a first diode D1 to provide a boosted output voltage Vbst to a load represented by load current I_load. An output capacitor Cout has a first terminal coupled to a second node 107, which is between first diode D1 and load current I_load, and a second terminal coupled to the lower rail. A feedback loop is coupled to the second node 107 and to the fourth pin P4 to provide a gate-driver supply voltage Vcc to DC/DC boost converter chip 101. In the embodiment shown in FIG. 1A, clamping circuit 109 is provided to clamp the boosted output voltage Vbst to a desired gate-driver supply voltage Vcc, although the need for a clamping circuit depends on the specific implementation. A second diode D2 is coupled between first node 105 and second node 107 in order to provide an initial voltage to both the feedback loop for gate-driver supply voltage Vcc and to the boosted output voltage Vbst. In one embodiment, both first diode D1 and second diode D2 are Schottky diodes.

In one embodiment, the elements shown of DC/DC boost converter 100A have the following values: battery resistance Rbat is 0.1Ω, inductor resistance Rind is less than or equal to 0.56Ω, input capacitance Cin is 10 µF, output capacitance Cout is 4.7 µF, battery voltage Vbat is equal to or greater than 2 V, and the boosted output voltage Vbst, which is between about 2.7 V and about 11.5 V, is clamped to provide a gate-driver supply voltage Vcc that is between about 1.7 V and about 6.2 V. When the battery voltage Vbat is at the minimum of 2.0 V, it follows that the minimum gate-driver supply voltage Vcc that can be provided to the gate of the low-side power FET M1 is 1.7 V, i.e., the battery voltage Vbat minus the diode drop across second diode D2.

In designing for the above noted values, one issue addressed was how to meet a target peak inductor current Ipeak of 500 mA when the gate-driver supply voltage Vcc is at a low value of 1.7 V. Table 1 below provides the threshold voltages for low-side power FET M1 at the corners of process and temperature:

TABLE 1

| Temperature | Threshold Voltage | | |
| --- | --- | --- | --- |
| | Strong | Nominal | Weak |
| −40° C. | 1.02 V | 1.28 V | 1.52 V |
| 27° C. | 0.9 V | 1.16 V | 1.4 V |
| 125° C. | 0.72 V | 0.98 V | 1.22 V |

At the worst corner, i.e., a weak transistor at a temperature of −40° C., the threshold voltage Vth is 1.52 V.

Table 2 provides a comparison of the peak inductor current Ipeak that can be achieved at various values of gate-driver supply voltages Vcc using a drain/source voltage Vds of 0.2 V at the worst corner for low-side power FET M1:

TABLE 2

| Vcc [V] | Ipeak [mA] |
| --- | --- |
| 1.7 | 44 |
| 1.8 | 86 |
| 1.9 | 137 |
| 2.0 | 191 |
| 2.1 | 243 |
| 2.2 | 293 |
| 2.3 | 339 |
| 2.4 | 382 |
| 2.5 | 422 |
| 2.6 | 459 |
| 2.7 | 492 |

As can be seen from Table 2, while the low-side power FET M1 can provide a current of 492 mA when the gate-driver supply voltage Vcc is 2.7 V, when gate-driver supply voltage Vcc is only 1.7 V, low-side power FET M1 can only provide a current of 44 mA. In other words, in order to meet a peak inductor current Ipeak of 500 mA, the size of the low-side power FET M1 needs to be increased by a factor of eleven or else a charge pump needs to be incorporated into the design to boost the gate voltage to 2.7 V. These alternatives both come with a price of much larger die size and lowered efficiency for DC/DC boost converter chip 101, while a strong desire exists to maintain low cost and high efficiency.

Rather than utilizing the prior art solutions, the current implementation performs a first peak inductor current gear-shifting method by setting the peak inductor current Ipeak to an initial peak value, which in one embodiment is less than or equal to about 40 mA. Using this initial peak value, the boosted output voltage Vbst of DC/DC boost converter 100A rises more slowly than would occur with a higher value of peak inductor current Ipeak, but the startup of DC/DC boost converter is guaranteed. Then, once boosted output voltage Vbst reaches a threshold output voltage, e.g., 3.0 V in one embodiment, the peak inductor current Ipeak can be shifted to the target peak value, e.g., 500 mA. Although this first peak inductor current gear-shifting method is primarily used during startup, if the boosted output voltage Vbst drops below the threshold output voltage, the initial peak value of peak inductor current Ipeak can be re-used until the boosted output voltage Vbst again rises above the threshold value.

A second peak inductor current gear-shifting method can be used when the load current changes. During operation of DC/DC boost converter 100A, load current I_load can vary by several orders of magnitude. When the load current drops, the switching frequency Fsw of DC/DC boost converter 100A slows in order to maintain a stable value for boosted output voltage Vbst. If the load current I_load drops too much, there is a risk that the switching frequency Fsw will drop into the audio band, where the switching can cause audible noise and interference with audio signals. For this reason it is desirable to keep the switching frequency Fsw higher than the audio band.

A traditional solution to a drop in the load current I_load is to provide a dummy load on the output to maintain the operation of switching frequency Fsw at a faster rate, which again reduces the efficiency of DC/DC boost converter 100A. In contrast, the disclosed embodiment decreases the value of the peak inductor current Ipeak in a stepwise fashion so that the switching frequency Fsw can be maintained above the audio band. When the load current I_load later increases, the value of peak inductor current Ipeak can be increased in a stepwise fashion to maintain the output voltage. Implementation of the disclosed second inductor current gear-shifting method can be better understood with reference to some of the control signals that are produced in a DC/DC boost converter and by understanding how these control signals relate to the switching of low-side power FET M1. The control signals will be explained with reference to FIG. 1B, which discloses where the control signals are produced, and to FIGS. 2A and 2B, which depict several of the control signals with reference to the inductor current.

Figure 1B:
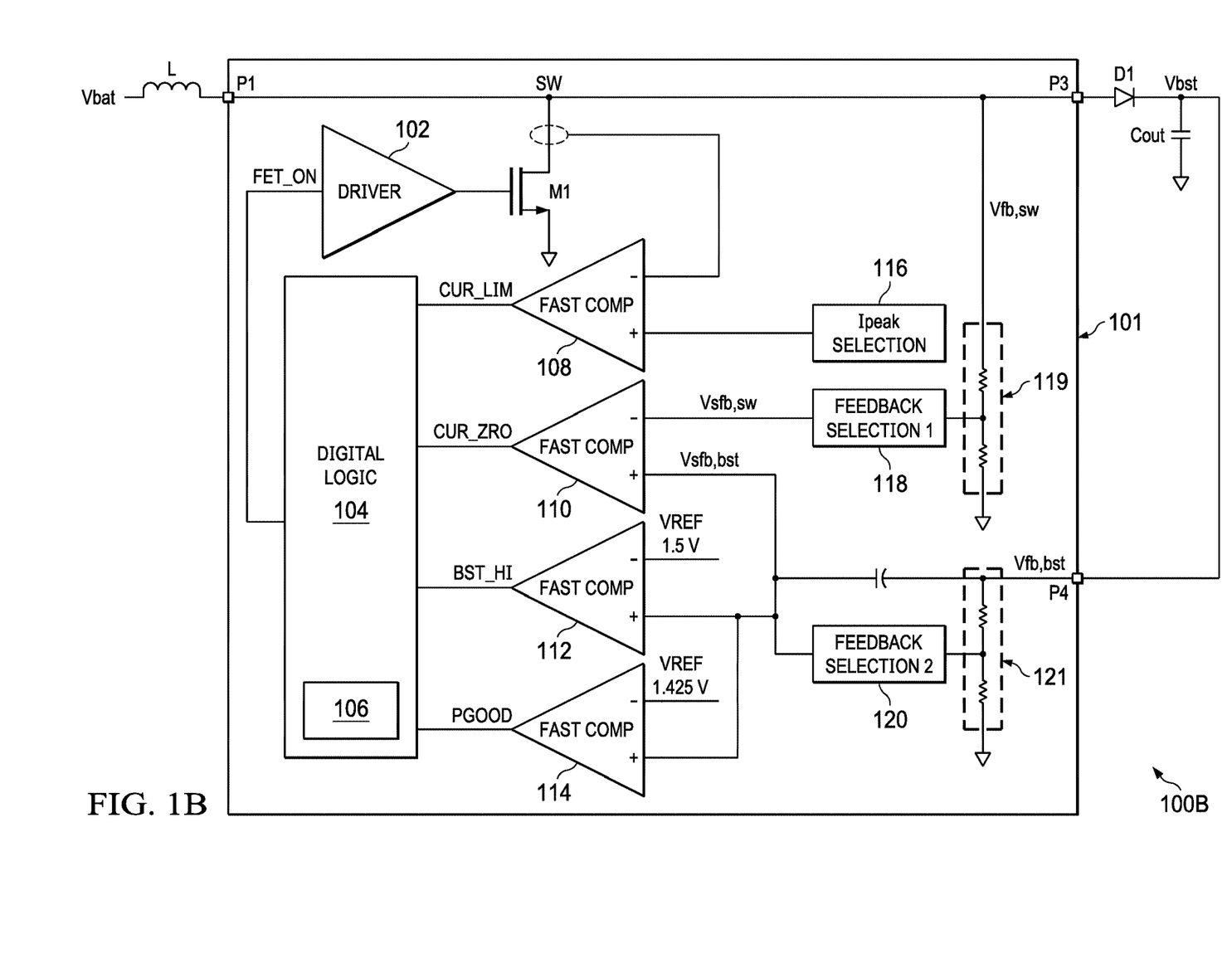
FIG. 1B depicts a block diagram of an example DC/DC boost converter in which the disclosed method of operation can be incorporated according to an embodiment of the disclosure.

FIG. 1B depicts a block diagram of an example DC/DC boost converter 100B in which the disclosed method of operation can be implemented. FIG. 1B is similar to FIG. 1A, but provides more details about DC/DC boost converter chip 101. Within DC/DC boost converter chip 101, switch-node SW is again located between first pin P1 and third pin P3 and low-side power FET M1 is coupled between switch-node SW and the lower rail. A gate driver circuit 102 is coupled to receive a FET-on signal FET_ON and to control low-side power FET M1 in response to the FET-on signal FET_ON.

Digital logic circuit 104, which in the current embodiment includes Ipeak gear-shifting circuit 106, dynamically determines the switching frequency Fsw of DC/DC boost converter 100B and creates the FET-on signal FET_ON. The switching frequency Fsw is determined by factors that include the load current I_load and the peak inductor current Ipeak. As mentioned previously, when the load current drops, the switching frequency Fsw of DC/DC boost converter 100B slows in order to maintain a stable value for boosted output voltage Vbst and care must be taken to ensure that the switching frequency Fsw does not drop into the audio range. Rather than monitoring the switching frequency Fsw directly, digital logic circuit 104 can monitor related indicators. In one embodiment, the idle-state time is monitored as explained below.

Inputs received by digital logic circuit 104 include signals from four comparators. A current-limit comparator 108 compares the current through low-side power FET M1, which is received on an inverting input, to a value that is set for peak inductor current Ipeak. A current value for peak inductor current Ipeak is provided to the non-inverting input of current-limit comparator 108 by Ipeak selection circuit 116. In one embodiment, a target peak value for peak inductor current Ipeak can be set in firmware and can have a value between 30 mA and 500 mA. It will be recognized that during the time when low-side power FET M1 is turned on, the current through low-side power FET M1 is the same as the current through inductor L. Accordingly, current-limit comparator 108 determines when the current through inductor L equals the peak inductor current Ipeak and provides the current limit signal CUR_LIM to signal that the inductor current I_ind has reached the peak inductor current Ipeak and that the low-side power FET can be turned off.

Zero-current comparator 110, boost-high comparator 112 and power-good comparator 114 each receive one or both of two feedback signals provided by first feedback selection circuit 118 and second feedback selection circuit 120. First feedback selection circuit 118 receives a switch-node feedback voltage Vfb,sw from switch-node SW via a first resistive divider 119, scales the switch-node feedback voltage Vfb,sw according to a target output voltage for boosted output voltage Vbst and provides a scaled switch-node feedback voltage Vsfb,sw. Second feedback selection circuit 120 receives a boosted feedback voltage Vfb,bst from boosted output voltage Vbst via a fourth pin P4 and a second resistive divider 121, scales the boosted feedback voltage Vfb,bst according to the target output voltage for boosted output voltage Vbst and provides the scaled boosted feedback voltage Vsfb,bst.

Zero-current comparator 110 receives the scaled switch-node feedback voltage Vsfb,sw on an inverting input and receives the scaled boosted feedback voltage Vsfb,bst on a non-inverting input. It can be noted that switch-node voltage Vsw is separated from boosted output voltage Vbst by one diode drop across second diode D2, but this difference disappears when the current through first diode D1 is zero. Zero-current comparator 110 is thus able to detect a zero crossing of the inductor current I_ind by determining when switch-node voltage Vsw is equal to 85% of boosted output voltage Vbst and sets zero current signal CUR_ZRO high when this condition is true. Zero current signal CUR_ZRO will remain high until the inductor current I_ind next reaches peak current limit Ipeak, as will be demonstrated.

Both boost-high comparator 112 and power-good comparator 114 receive scaled boosted feedback voltage Vsfb,bst on a respective non-inverting input. Boost-high comparator 112 compares the scaled boosted feedback voltage Vsfb,bst to a first reference voltage that represents the target output voltage. In one embodiment the first reference voltage is 1.5 V. Using the scaled voltages, boost-high comparator 112 effectively compares the boosted output voltage Vbst to the target output voltage and sets a boosted-voltage-high signal BST_HI to a high value when the boosted output voltage Vbst is greater than the target output voltage.

Power-good comparator 114 compares the scaled boosted feedback voltage Vsfb,bst to a second reference voltage that represents a rising threshold value. In one embodiment the second reference voltage is 1.425 V, i.e., 95% of the target output voltage of 1.5 V. Although not specifically shown, power-good comparator 114 also compares the scaled boosted feedback voltage Vsfb,bst to a third reference voltage that represents a falling threshold value. In one embodiment the third reference voltage is 1.275 V, which is 85% of 1.5 V. The power-good comparator 114 provides a power good signal PGOOD that indicates to the digital logic circuit 104 that the scaled boosted feedback voltage is between the second reference voltage and the third reference voltage, i.e. that the power supply is within target ranges.

Figure 2A:
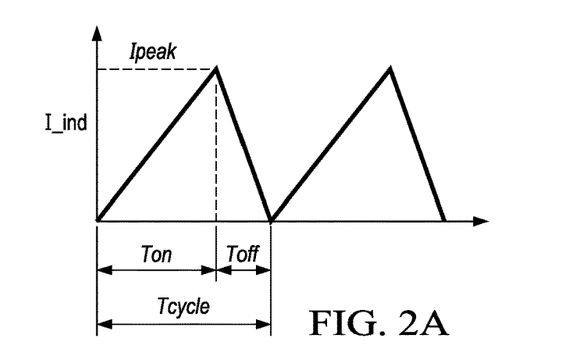
FIG. 2A depicts the inductor current waveform of a DC/DC boost converter during continuous conduction mode.
Figure 2B:
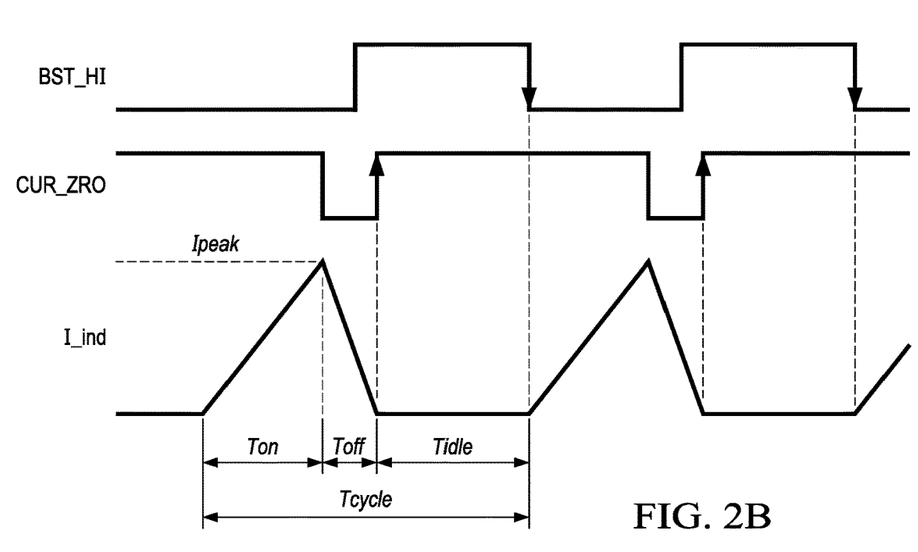
FIG. 2B depicts several waveforms of a DC/DC boost converter during discontinuous conduction mode.

FIGS. 2A and 2B graphically illustrate the inductor current during two different modes of operation in order to show how the DC/DC boost converter 100B can drop into the audio band. FIG. 2A depicts the inductor current I_ind during continuous conduction mode (CCM) and FIG. 2B depicts the inductor current I_ind during discontinuous conduction mode (DCM). During CCM in FIG. 2A, low-side power FET M1 is turned on during an on-state time Ton and inductor current I_ind rises at a constant rate until the inductor current I_ind reaches the peak inductor current Ipeak. At this point low-side power FET M1 is turned off for an off-state time Toff while the inductor current I_ind falls steadily until inductor current I_ind reaches zero. At the point at which inductor current I_ind reaches zero during CCM, it is determined that further charging is needed immediately and the cycle starts again. In CCM, the inductor current I_ind is either rising or falling at all times and cycle time Tcycle is equal to Ton plus Toff.

In contrast, during DCM as seen in FIG. 2B, inductor current I_ind rises during on-state time Ton to reach peak inductor current Ipeak, then falls during off-state time Toff until inductor current I_ind reaches zero. Once inductor current I_ind reaches zero, a determination is made that further current is not needed for some period of time. This determination is made by checking the value of boosted-voltage-high signal BST_HI when zero current signal CUR_ZRO goes high. If boosted-voltage-high signal BST_HI is high, this indicates that no additional current is needed and an idle-state time Tidle ensues until boosted-voltage-high signal BST_HI again is low. During DCM the cycle time Tcycle is equal to Ton plus Toff plus Tidle. When DC/DC boost converter 100B is operating in CCM, the design will ensure that the switching frequency Fsw is greater than the audio band; however when idle-state time Tidle becomes too large, the switching frequency Fsw may be in danger of dropping into the audio band.

Thus, Ipeak gear-shifting circuit 106 can monitor the values of boosted-voltage-high signal BST_HI and zero current signal CUR_ZRO to determine the length of idle-state time Tidle, if any is present. In one embodiment, responsive to Ipeak gear-shifting circuit 106 determining that the zero current signal CUR_ZRO has a rising edge and that boosted-voltage-high signal BST_HI has a high value, Ipeak gear-shifting circuit 106 starts counting clock cycles until boosted-voltage-high signal BST_HI has a falling edge. In one embodiment, an 8 MHz oscillator clock is used to measure the idle-state time Tidle.

When the idle-state time Tidle is greater than a first idle-state threshold, e.g., 10 μs, the value of peak inductor current Ipeak is reduced by a decrement amount according to rules that govern the process. In one embodiment, the decrement amount is applied if a series of N consecutive cycles each have a respective idle-state time Tidle that is greater than the first idle-state threshold. When a series of N consecutive cycles are required to trigger a decrement, a single cycle that has an idle-state time Tidle that is greater than a second idle-state threshold (e.g., 32 μs) can also trigger a decrement of the peak inductor current Ipeak. The peak inductor current Ipeak can be decremented in this manner until it is determined that the possibility of dropping into the audio band is no longer a threat.

When the peak inductor current Ipeak has been decremented to a value lower than the target peak value, DC/DC boost converter 100B needs to monitor whether the boosted output voltage Vbst remains adequate for the demands of the load. When the load current I_load does increase, the boosted output voltage Vbst will fall. If Ipeak gear-shifting circuit 106 detects that boosted output voltage Vbst has fallen by a given voltage drop, peak inductor current Ipeak is increased by an increment amount. The peak inductor current Ipeak can be incremented in a stepwise manner until the boosted output voltage Vbst is again stabilized at the target output voltage. In one embodiment, peak inductor current Ipeak is incremented each cycle that boosted output voltage Vbst is less than 85% of a target value, e.g., 11.5 V. It is important to ensure that boosted output voltage Vbst is as constant as possible. For this reason, incrementing the value of peak inductor current Ipeak will generally occur at a faster rate than decrementing peak inductor current Ipeak.

The use of Ipeak gear-shifting in a DC/DC boost converter as shown in FIG. 1A and FIG. 1B is effective because of the relationship of boost converter cycle time Tcycle to the peak inductor current Ipeak and the load current I_load:

$$Fsw \propto \frac{(Ipeak)^2}{I\_load} \quad \text{Equation 1}$$

where Fsw is the switching frequency and is the inverse of the cycle time Tcycle.

Equation 1 demonstrates that reducing peak inductor current Ipeak by a factor of ten can compensate for the reduction of load current I_load by a factor of one hundred!

The relationship between the inductor voltage V_ind and the inductor current I_ind can be expressed by the following equation:

$$V\_ind = L\frac{dI\_ind}{dt} \quad \text{Equation 2}$$

where L is the inductance of the inductor. Equation 2 can be rewritten as:

$$dt = L\frac{dI\_ind}{V\_ind} \quad \text{Equation 3}$$

The on-state time Ton for low-side power FET M1 can be expressed by the following equation:

$$Ton = \frac{L*\Delta I\_ind}{V\_ind} = \frac{L*I_{peak}}{Vin - I\_ind*Rind - Rdson*I\_ind} \quad \text{Equation 4}$$

It can be noted that load current I_ind is generally linear between zero and the peak inductor current Ipeak in both an on-state and an off-state, and can be replaced with Ipeak/2 for a first-order approximation in calculations. For an inductance L equal to 33 μH, a peak inductor current Ipeak equal to 500 mA and a minimum value for the expression (Vin-I_ind*Rind−Rdson*I_ind) equal to 1.5V, the value of on-state time Ton is equal to 11 µs. The value of off-state time Toff is expressed by the equation:

$$Toff = \frac{L * \Delta I\_ind}{V\_ind} = \frac{L * Ipeak}{(Vout - Vin + Rind * I\_ind + Vd)} \quad \text{Equation 5}$$

For an inductance equal to 33 µH, an inductor peak current equal to 500 mA, an output voltage Vout equal to 11.5 V and a minimum value for the expression (Vout−Vin+Rind*I_ind+Vd) equal to 10 V, off-state time Toff is equal to 1.65 µs. In total, the cycle time Tcycle is equal to Ton plus Toff of 12.65 µs.

During CCM mode, the cycle time Tcycle, which is equal to on-state time Ton plus off-state time Toff can be expressed by the following:

$$Tcycle = \frac{L * Ipeak}{Vin - I\_ind * Rload - Rdson * I\_ind} + \frac{L * Ipeak}{(Vout - Vin + Rind * I\_ind + V_d)} \quad \text{Equation 6}$$

which can be rewritten as:

$$L * \frac{2 * I\_load}{\eta} * \frac{Vout}{Vin} * \left[ \frac{1}{Vin - I\_ind * Rind - Rdson * I\_ind} + \frac{1}{(Vout - Vin + Rind * I_{ind} + Vd)} \right] \quad \text{Equation 7}$$

wherein η is the boost efficiency. Neglecting the core loss of inductor L, boost efficiency η can be expressed as:

$$\eta = \frac{Pout}{Pin} = \frac{Vout}{Vin} * \frac{Toff}{Ton + Toff} = \frac{Vout}{Vin} * \frac{Vin - (Rind + Rdson) * I\_ind}{(Vout - Rdson * I_{ind} + Vd)} \quad \text{Equation 8}$$

During DCM mode, the cycle time Tcycle is equal to on-state time Ton plus off-state time Toff plus idle-state time Tidle and can be expressed as:

$$Tcycle = \quad \text{Equation 9}$$
$$\frac{Ipeak/2}{I\_load} * Toff = \frac{Ipeak/2}{I\_load} * \frac{L * Ipeak}{Vout - Vin + Rind * \frac{Ipeak}{2} + Vd}$$

With R_ind*Ipeak/2, which is much less than Vout−Vin+Vd in the denominator, the cycle time Tcycle is proportional to Ipeak²/I_load. It can also be noted that cycle time Tcycle is also proportional to the inductance L. A smaller inductance means a higher switching frequency, although the inductance needs to meet a saturation current greater than peak inductor current Ipeak.

Figure 3:
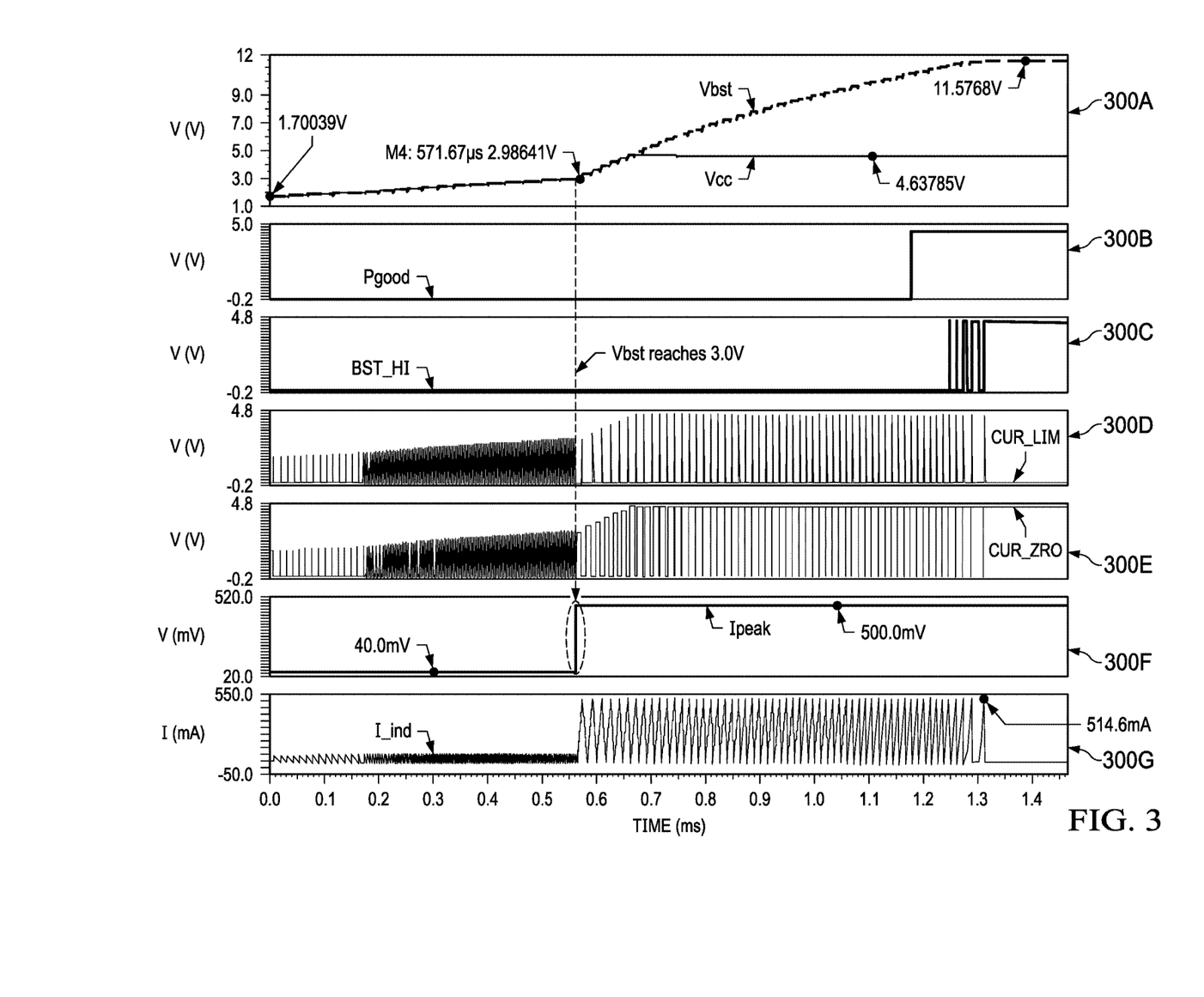
FIG. 3 depicts various signals of a DC/DC boost converter during startup according to an embodiment of the disclosure.
Figure 4:
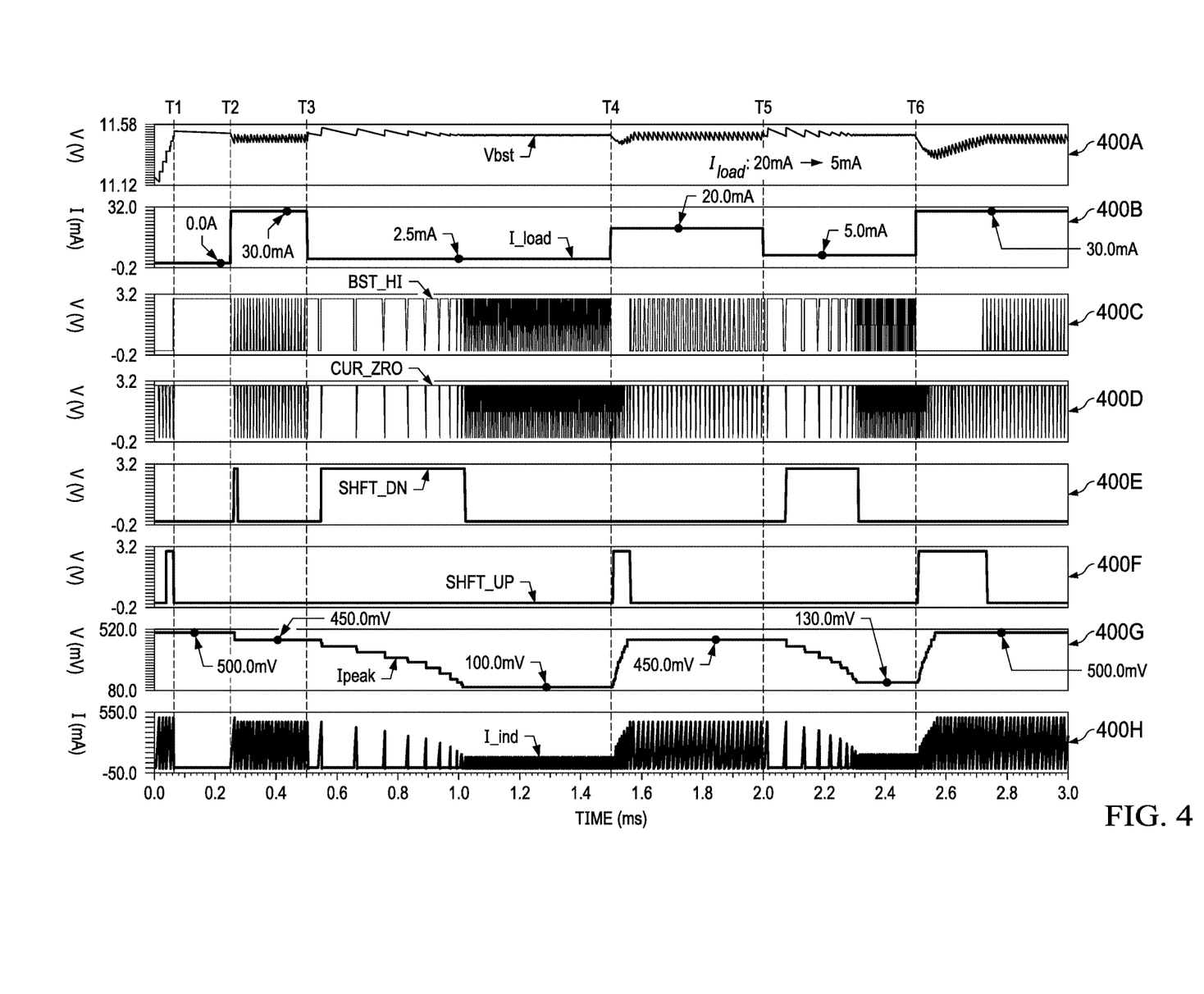
FIG. 4 depicts various signals as the load changes during operation of a DC/DC boost converter according to an embodiment of the disclosure.
Figure 5:
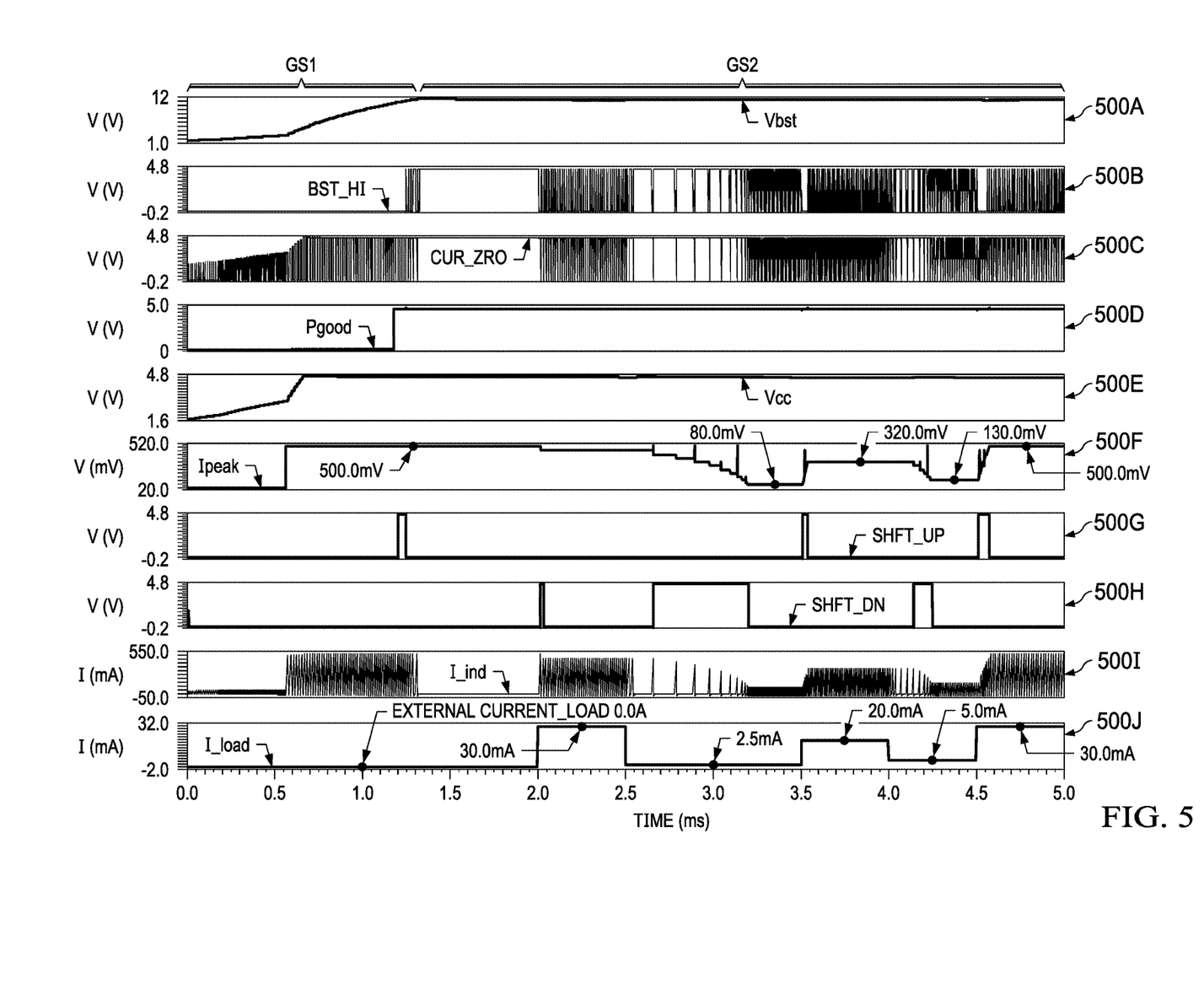
FIG. 5 depicts various signals during a simulation of a DC/DC boost converter according to an embodiment of the disclosure.

Having looked at the mathematics involved, we turn now to look at the signals on DC/DC boost converter 100B during the two Ipeak gear-shifting methods, which are shown in FIGS. 3-5. FIG. 3 depicts a number of waveforms from a DC/DC boost converter in which the disclosed first Ipeak gear-shifting method has been implemented. Graph 300A depicts both gate-driver supply voltage Vcc and boosted output voltage Vbst. Graph 300B depicts the power good signal Pgood; graph 300C depicts the boosted-voltage-high signal BST_HI; graph 300D depicts the current limit signal CUR_LIM; graph 300E depicts the zero current signal CUR_ZRO; graph 300F depicts the value of peak inductor current Ipeak; and graph 300G depicts the inductor current I_ind. It can be noted in this and the following figures that although the peak inductor current Ipeak is discussed in milliamperes, the measurement is shown as an equivalent number of millivolts.

At startup, gate-driver supply voltage Vcc and boosted output voltage Vbst in (300A) both start at 1.7 V, which is the supply voltage from the battery minus a diode drop. The peak inductor current Ipeak (300F) is set to an initial peak value of 40 mA. The current limit signal CUR_LIM (300D) and the zero current signal CUR_ZRO (300E) begin operating to control the operation of low-side power FET M1, which causes a small amount of the inductor current I_ind (300G) to be provided at the output pin each time low-side power FET M1 is turned off and consequently causes both gate-driver supply voltage Vcc and boosted output voltage Vbst (300A) to be incremented. This continues until boosted output voltage Vbst reaches a threshold output voltage, which in the simulation shown was 3.0 V.

When boosted output voltage Vbst (300A) reaches the threshold output voltage, the peak inductor current Ipeak (300F) is set to the target peak value, which in this embodiment is 500 mA. This causes the inductor current I_ind (300G) to have a much wider swing as the amount of inductor current provided when low-side power FET M1 is turned off increases to the new value of peak inductor current Ipeak; both gate-driver supply voltage Vcc and boosted output voltage Vbst now increase at a faster rate. In this embodiment, gate-driver supply voltage Vcc is clamped at 4.6 V, but boosted output voltage Vbst continues to climb to a target output voltage of about 11.5 V. At 85% of the target output voltage, the power good signal Pgood (300B) goes high and at 95% of the target output value, boosted-voltage-high signal BST_HI (300C) begins operating and indicates whether any idle time is necessary.

FIG. 4 depicts a number of waveforms from a DC/DC boost converter in which the disclosed second Ipeak gear-shifting method has been implemented. Graph 400A depicts the boosted output voltage Vbst; graph 400B depicts the load current I_load as it varied to test the DC/DC boost converter operation; graph 400C depicts the boosted-voltage-high signal BST_HI; graph 400D depicts zero current signal CUR_ZRO; graph 400E depicts a shift downward signal SHFT_DN; graph 400F depicts a shift upward signal SHFT_UP; graph 400G depicts the peak inductor current Ipeak as this value is shifted; and graph 400H depicts the inductor current I_ind.

At time T1, the boosted output voltage Vbst (400A) has come up to a target output voltage, but the load current I_load is 0 Amps. As zero current signal CUR_ZRO (400D) has a rising edge, it is determined that boosted-voltage-high signal BST_HI (400C) is high; boosted-voltage-high signal BST_HI remains high until time T2. Because of the extended period in which boosted-voltage-high signal BST_HI is high, the Ipeak gear-shifting circuit 106 determines that one cycle exceeded the second preset time and a shift downward signal SHFT_DN (400E) is activated, causing inductor peak current Ipeak (400G) to be decreased from 500 mA to 450 mA. At time T2, the load current I_load (400B) rises to 30.0 mA and regular switching of the DC/DC boost converter resumes at the peak inductor current Ipeak of 450 mA (400F), as shown by the boosted-voltage-high signal BST_HI (400C) and zero current signal CUR_ZRO (400D).

At time T3, the load current I_load drops from 30.0 mA to 2.5 mA, and the switching frequency slows to compensate for the lowered need for current, as shown by the longer periods of boosted-voltage-high signal BST_HI (400C) and the zero current signal CUR_ZRO (400D) remaining at the high state. Shortly afterwards, the logic circuit detects the increased idle time and sets shift downwards signal SHFT_DN (400E) high. During the time that the shift downwards signal SHFT_DN is high, the Ipeak gear-shifting circuit 106 adjusts the peak inductor current Ipeak (400G) downward, in this instance at each cycle, and the switching frequency increases until the shift downwards signal SHFT_DN (400E) is finally set low again after the value of peak inductor current Ipeak (400G) has been reduced to 100 mA.

At time T4, the load current I_load (400B) increases from 2.5 mA to 20 mA, causing boosted output voltage Vbst (400A) to drop. This change to boosted output voltage Vbst is quickly detected and the shift upwards signal SHFT_UP (400F) goes high. In response, the Ipeak gear-shifting circuit 106 adjusts the peak inductor current Ipeak (400G) upwards until the peak inductor current Ipeak reaches 450 mA, at which point the boosted output voltage Vbst (400A) is back to the target output voltage. It can be noted that the peak inductor current Ipeak was increased from 100 mA to 450 mA in a much shorter time than was used to decrease the peak inductor current Ipeak by the same amount, as maintaining the boosted output voltage Vbst at a constant value is a high priority.

At time T5 load current I_load (400B) again drops, this time from 20 mA to 5 mA. As the decreased switching cycle is detected, the shift downwards signal SHFT_DN (400E) is again set high and the peak inductor current Ipeak (400G) is again decremented downwards until the switching frequency increases to a frequency that will not cause audible noise. In the example shown, peak inductor current Ipeak is decreased from 450 mA to 130 mA. It can be seen by comparing the first downward shift after time T3 and the second downward shift after time T5 that how quickly the peak inductor current Ipeak is decremented depends on the current cycle time and that as the cycle time decreases, the rate of change increases.

At time T6, the load current I_load (400B) increases again, from 5 mA to 30 mA and pulls the boosted output voltage Vbst (400A) low. As soon as the voltage drop is detected, the shift upwards signal SHFT_UP (400F) is set high, initiating the Ipeak gear-shifting circuit 106 to increment the peak inductor current Ipeak. Because the voltage drop at time T6 was larger than the voltage drop at time T4, boosted-voltage-high signal BST_HI (400C) remains low for a longer period, signaling the continuing need to bring the boosted output voltage Vbst (400A) back up to the nominal value. Although the peak inductor current Ipeak (400G) is returned to the target value of 500 mA quickly, recovery of boosted output voltage Vbst takes longer, so boosted-voltage-high-signal BST_HI (400C) remains low and shift upwards signal SHFT_UP (400F) remains high until boosted output voltage Vbst (400A) returns to about 11.5 V.

FIG. 5 depicts a number of waveforms from a DC/DC boost converter in which both the disclosed first and second Ipeak gear-shifting methods have been implemented, emphasizing the fact that it is within the scope of the disclosure to implement either one or both of the disclosed gear-shifting methods in a DC/DC boost converter. Graph 500A depicts boosted output voltage Vbst; graph 500B depicts the boosted-voltage-high signal BST_HI; graph 500C depicts zero current signal CUR_ZRO; graph 500D depicts the power good signal Pgood; graph 500E depicts gate-driver supply voltage Vcc; graph 500F depicts peak inductor current Ipeak; graph 500G depicts shift upwards signal SHFT_UP; graph 500H depicts the shift downwards signal SHFT_DN; graph 500I depicts inductor current I_ind; and graph 500J depicts load current I_load. During a first time period GS1, the first Ipeak gear-shifting method is demonstrated and during a second time period GS2, the second Ipeak gear-shifting method is demonstrated.

At the beginning of the first time period GS1, the boosted output voltage Vbst (500A) is at a minimum value of about 1.7 V and gate-driver supply voltage Vcc (500E) has the same value. Peak inductor current Ipeak (500F) has an initial peak value of about 40 mA, such that as switching of the low-side power transistor M1 begins, boosted output voltage Vbst (500A) and gate-driver supply voltage Vcc (500E) rise in slow increments. Load current I_load (500J) is zero during this period. Once the boosted output voltage Vbst reaches the threshold output voltage of about 3 V at about 0.55 msec into the simulation, peak inductor current Ipeak (500F) is set to the target peak value of 500 mA and the boosted output voltage Vbst (500A) rises more quickly to a target output voltage of about 11.5 V; gate-driver supply voltage Vcc (500E) follows the boosted output voltage Vbst up to a value of about 4.7 V where gate-driver supply voltage Vcc is clamped. Once boosted output voltage Vbst (500A) reaches 85% of the target output voltage, power good signal Pgood (500D) goes high and the logic circuits begin to operate, so that shift-upwards signal SHFT_UP (500G) goes high. Since the peak inductor current Ipeak (500F) is already set to the target peak value of 500 mA, no further action is taken to raise the peak inductor current at this time.

The DC/DC boost converter 100B now enters the second time period GS2. At 2 ms into the simulation, the load current I_load (500J) goes from zero to 30 mA. Because a long idle-state time was observed in the previous cycle (see, e.g., boosted-voltage-high signal BST_HI (500B)), shift-downwards signal SHFT_DN (500H) goes high for a short period of time and the peak inductor current Ipeak (500F) is decremented to 450 mA. At 2.5 ms into the simulation, the load current I_load (500J) drops from 30 mA to 2.5 mA and the switching frequency slows, as reflected in the boosted-voltage-high signal BST_HI (500B). After several switching cycles, the condition is recognized and the shift downwards signal SHFT_DN (500H) is set high and peak inductor current Ipeak (500F) is decremented over a period of about 0.55 msec from 450 mA to 80 mA.

At 3.5 msec, load current I_load (500J) rises to a value of 20 mA, shift upwards signal SHFT_UP (500G) goes high briefly and the peak inductor current Ipeak (500F) is incremented up to 320 mA to ensure the boosted output voltage Vbst (500A) remains steady. At 4.0 msec, load current I_load (500J) drops from 20 mA to 5.0 mA; after several switching cycles, shift downwards signal SHFT_DN (500H) goes high and peak inductor current Ipeak (500F) is decremented in a series of steps to a value of 130 mA. At 4.5 msec, load current I_load (500J) again rises to 30.0 mA, shift upwards signal SHFT_UP (500G) goes high and peak inductor current Ipeak (500F) is incremented to the target peak value of 500 mA.

Figure 6:
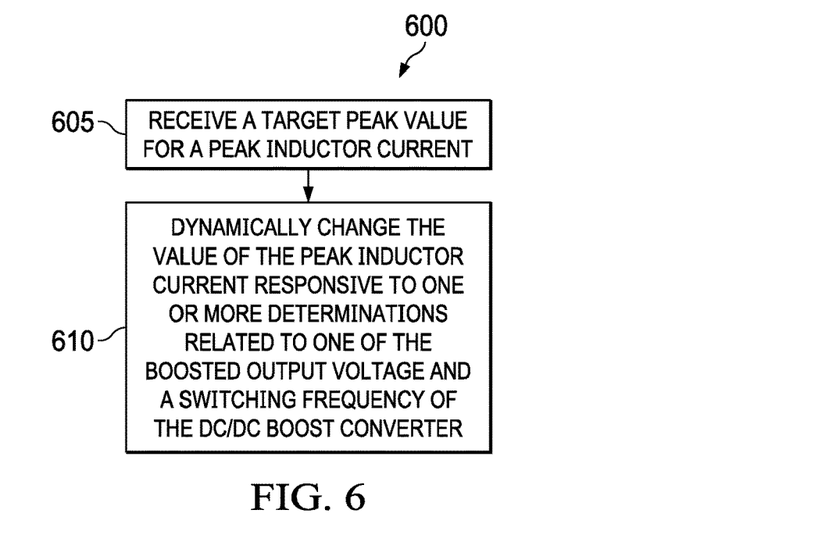
FIG. 6 depicts an overall method of operating a DC/DC boost converter according to an embodiment of the disclosure.
Figure 6A:
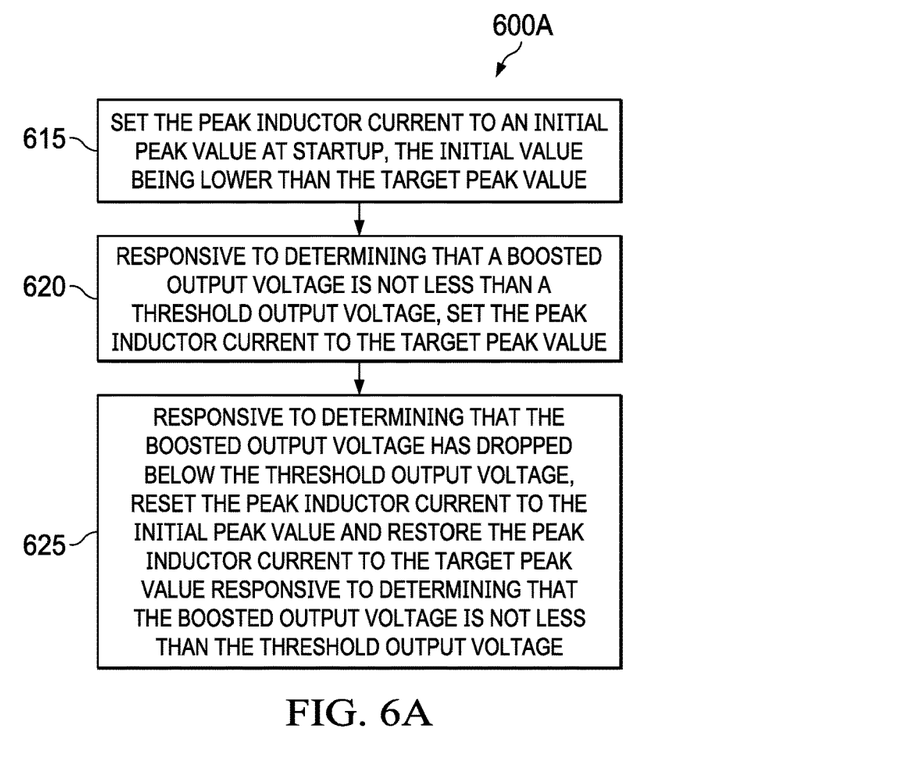
FIG. 6A depicts a first peak inductor current gear-shifting method according to an embodiment of the disclosure.
Figure 6B:
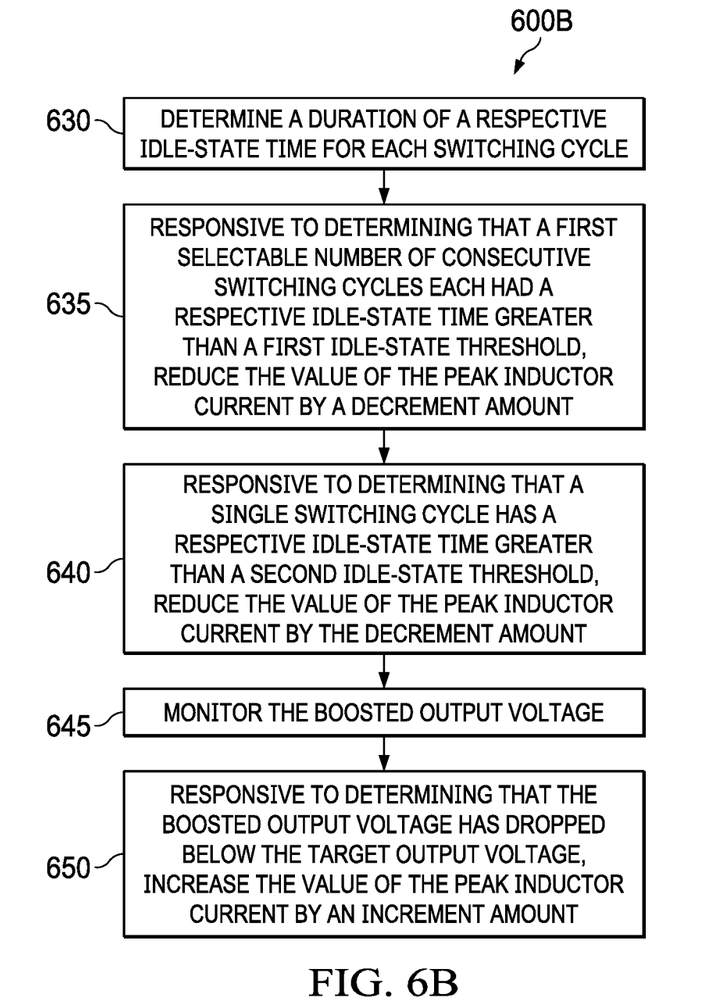
FIG. 6B depicts a second peak inductor current gear-shifting method according to an embodiment of the disclosure.

FIG. 6 depicts an overall method 600 of operating a DC/DC boost converter according to an embodiment of the disclosure; FIG. 6A and FIG. 6B further define how elements of method 600 are performed. FIG. 6A depicts the first Ipeak gear-shifting method 600A; and FIG. 6B depicts the second Ipeak gear-shifting method 600B. Method 600 begins with receiving 605 a target peak value for the peak inductor current Ipeak. The target peak value can be provided in a number of ways, including being hardwired into the circuitry, although more generally the target peak value is provided in firmware or else programmed into the system using a pin input or register input. In the embodiments shown herein, the target peak value has been 500 mA, although this is only an example and not a limitation.

The method then continues with dynamically changing 610 the value of the peak inductor current Ipeak responsive to one or more determinations related to one of the boosted output voltage and a switching frequency of the DC/DC boost converter. As has been seen in the previous discussions, the first Ipeak gear-shifting method relies on the value of the boosted output voltage Vbst in order to raise the peak inductor current Ipeak to the target peak value, while the second gear-shifting method utilizes the switching frequency, or surrogates for the switching frequency such as idle-state time or total switching cycle time, to adjust the peak inductor current Ipeak downwards and uses the boosted output voltage Vbst to adjust the peak inductor current Ipeak upwards.

In method 600A, dynamically changing the value of the peak inductor current Ipeak includes setting 615 the peak inductor current to an initial peak value at startup, the initial peak value being lower than the target peak value. In one embodiment, the initial peak value is 40 mA and the target peak value is 500 mA. The method then continues with setting 620 the peak inductor current Ipeak to the target peak value responsive to determining that the boosted output voltage is not less than a threshold output voltage. In one embodiment, the threshold output voltage is 3.0 V, which when used as the gate voltage for low-side NFET M1 can provide the target peak value for the inductor peak current Ipeak. Finally, responsive to determining that the boosted output voltage has dropped below the threshold output voltage, the Ipeak gear-shifting circuit can reset 625 the peak inductor current Ipeak to the initial peak value and then restore the peak inductor current Ipeak to the target peak value responsive to determining that the boosted output voltage is not less than the threshold output voltage.

In method 600B, dynamically changing the value of the peak inductor current includes determining 630 the duration of a respective idle-state time for each switching cycle. The value of the peak inductor current Ipeak can be reduced 635 by a decrement amount responsive to determining that a first selectable number of consecutive switching cycles each had a respective idle-state time greater than a first idle-state threshold, e.g., 10 μsec. The value of the peak inductor current Ipeak can also be reduced 640 responsive to determining that a single switching cycle has a respective idle-state time greater than a second idle-state threshold, e.g., 32 μsec. The boosted output voltage is also monitored 645 to determine whether the boosted output voltage is remaining at the target output voltage. Responsive to determining that the boosted output voltage has dropped below the target output voltage, the value of the peak inductor current Ipeak is increased 650 by an increment amount unless the peak inductor current is already at the target peak value.

Figure 7:
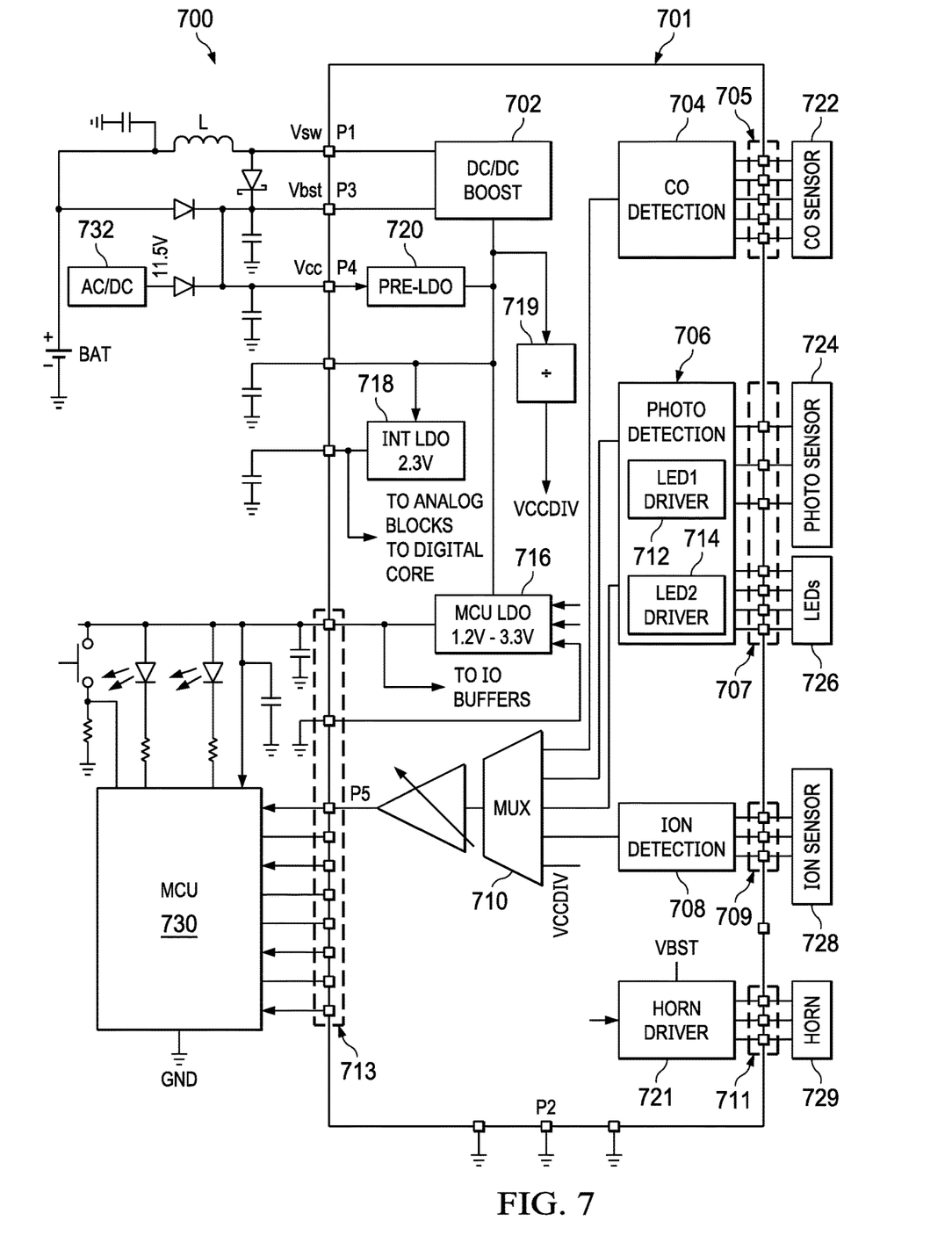
FIG. 7 depicts an example of a smoke detector that incorporates a DC/DC boost converter according to an embodiment of the disclosure.

FIG. 7 depicts a block diagram of a smoke detector 700 that incorporates a DC/DC boost converter 702 according to an embodiment of the disclosure. Smoke detector 700 includes an IC chip 701 on which a number of circuits are implemented. IC chip 701 includes DC/DC boost converter 702, which can be implemented using the hardware disclosed in DC/DC boost converter chip 101 and the disclosed Ipeak gear-shifting methods as discussed in methods 600, 600A and 600B. IC chip 701 also includes a carbon monoxide detection circuit 704, a photo-detection circuit 706, an ion detection circuit 708, and a horn driver 721. In one embodiment, photo-detection circuit 706 also includes a first light-emitting diode (LED) driver 712 and a second LED driver 714. Carbon monoxide detection circuit 704 is coupled to a first plurality of pins 705; photo-detection circuit 706 is coupled to a second plurality of pins 707; ion detection circuit 708 is coupled to a third plurality of pins 709; and horn driver 721 is coupled to a fourth plurality of pins 711. Multiplexor 710 can receive input signals from each of carbon monoxide detection circuit 704, photo-detection circuit 706 and ion detection circuit 708.

DC/DC boost converter 702 is coupled to first pin P1 to receive power from battery BAT through inductor L and to third pin P3 to provide boosted output voltage Vbst. The connection to second pin P2 is not specifically shown. Third pin P3 is also coupled to fourth pin P4, which provides the boosted output voltage Vbst to low dropout (LDO) regulator 720. Pin P4 can also be coupled to an AC/DC converter 732, which can provide an alternative to the voltage supplied by battery BAT. LDO regulator 720 provides the gate-driver supply voltage Vcc to the IC chip 701. The gate-driver supply voltage Vcc is distributed to DC/DC boost converter 702, where the voltage may be clamped, and to microcontroller (MCU) LDO 716, internal LDO 718 and Vcc divider 719. MCU LDO 716 provides a supply voltage to MCU 730 and the I/O buffers (not specifically shown); internal LDO 718 provides a supply voltage to internal circuits such as the data core and the analog blocks, e.g., the carbon monoxide detection circuit 704, photo-detection circuit 706 and ion detection circuit 708; and Vcc divider 719 provides a supply voltage to multiplexor 710. Horn driver 721 can be provided to drive a horn 729.

In smoke detector 700, carbon monoxide detection circuit 704 is coupled to carbon monoxide sensor 722 through the first plurality of pins 705; photo-detection circuit 706, which can include first LED driver 712 and second LED driver 714, is coupled to photo sensor 724 and LEDs 726 through the second plurality of pins 707; ion detection circuit 708 is coupled to ion sensor 728 through the third plurality of pins 709; and horn driver 721 is coupled to a horn 729 through the fourth plurality of pins 711. The carbon monoxide sensor 722, photo sensor 724 and ion sensor 728 collect the information needed to detect smoke and carbon monoxide in the area, while horn 729 provides a loud audible alert when smoke or carbon monoxide are detected. IC chip 701 is also coupled to MCU 730 though a fifth plurality of pins 713, with IC chip 701 supplying both power and information to MCU 730 and receiving instructions to control various aspects of operation of smoke detector 700.

Applicants have disclosed a method of operating a DC/DC boost converter that dynamically changes the peak inductor current Ipeak to accommodate the changing needs of the DC/DC boost converter. The peak inductor current Ipeak can be changed during startup of the IC chip, as well as anytime either the load current falls, which can drop the switching frequency into the audio range, or the boosted output voltage falls, indicating that the peak inductor current Ipeak may be too low. Advantages can include one or both of power savings and area savings. Area savings can come from the size of one or both of the low-side power FET M1 and the gate driver circuit 102. Savings in power consumption can occur during startup or when the DC/DC boost converter is lightly loaded, as compared to using a dummy current load to maintain the switching frequency above the audio band.

Although various embodiments have been shown and described in detail, the claims are not limited to any particular embodiment or example. None of the above Detailed Description should be read as implying that any particular component, element, step, act, or function is essential such that it must be included in the scope of the claims. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

What is claimed is:

1. An electronic device comprising a DC/DC boost converter, the DC/DC boost converter comprising:
    a voltage source providing a DC voltage;
    an inductor having first and second inductor terminals, the first inductor terminal coupled to the voltage source;
    a power N-type field effect transistor (NFET) having first and second current terminals and a control terminal, the first current terminal coupled to the second inductor terminal, and the second current terminal coupled to ground;
    a diode having a cathode and an anode, the anode coupled to the first current terminal, and the cathode providing a boosted output voltage;
    a digital logic circuit having a digital logic input and a digital logic output, the digital logic input coupled to the cathode, and the digital logic output coupled to the control terminal, the digital logic circuit configured to determine a switching frequency of the NFET, and to determine a duration of a respective idle-state time for a respective switching cycle of the NFET, the digital logic circuit including an Ipeak gear-shifting circuit that is configured to reduce a peak inductor current in response to a number of idle-state times exceeding an idle-state threshold.

2. The electronic device of claim 1, wherein the Ipeak gear-shifting circuit is configured to set the peak inductor current to an initial peak value at startup, and to set the peak inductor current to a target peak value in response to the boosted output voltage being at least equal to a threshold output voltage, the target peak value being greater than the initial peak value.

3. The electronic device of claim 2, wherein the Ipeak gear-shifting circuit is further configured to set the peak inductor current to the initial peak value in response to the boosted output voltage dropping below the threshold output voltage, and to set the peak inductor current to the target peak value in response to the boosted output voltage being at least equal to the threshold output voltage.

4. The electronic device of claim 1, wherein the idle-state time is a first idle-state time, and the Ipeak gear-shifting circuit reduces the peak inductor current in response to a respective switching cycle having an idle-state time that exceeds a second idle-state threshold.

5. The electronic device of claim 4, wherein the Ipeak gear-shifting circuit increases the peak inductor current in response to the boosted output voltage dropping below a target output voltage.

6. The electronic device of claim 1-4, wherein determining the duration of the respective idle-state time comprises:
    for each respective switching cycle, monitoring a boosted-voltage-high signal and a zero current signal, the boosted-voltage-high signal being set high when the boosted output voltage is greater than a target output voltage, and the zero current signal being set high when an inductor current is zero and being set low when the inductor current is at the peak inductor current; and
    counting the respective idle-state time until the boosted-voltage-high signal is low in response to a rising edge of the zero current signal and the boosted-signal-high signal being high.

7. The electronic device of claim 6, further comprising:
    a zero-current comparator having first and second zero comparator inputs and a zero comparator output, the first zero comparator input coupled to a first scaled boosted feedback voltage terminal, and the second zero comparator input coupled to a second scaled boosted feedback voltage terminal, and the zero comparator output configured to provide the zero current signal; and
    a boost-high comparator having a first boost comparator input, second boost comparator input and a boost comparator output, the first boost comparator input coupled to the second scaled boosted feedback voltage terminal, the second boost comparator input coupled to a first reference voltage terminal, and the boost comparator output configured to provide the boosted-voltage-high signal.

8. The electronic device of claim 7, further comprising:
    a current-limit comparator having a current-limit comparator output, and configured to compare a current through the NFET to the peak inductor current and provide a current limit signal at the current-limit comparator output; and
    a power-good comparator having first, second and third power comparator inputs and a power comparator output, the first power comparator input coupled to the second scaled boosted feedback voltage terminal, the second power comparator input coupled to a second reference voltage terminal, and the third power comparator input coupled to a third reference voltage terminal, the power comparator output providing a power good signal that indicates when the scaled boosted feedback voltage is between the second reference voltage and the third reference voltage.

9. The electronic device of claim 1, wherein the electronic device comprises an integrated circuit (IC) chip on which the power NFET, the gate driver and the digital logic circuit are fabricated.

10. The electronic device of claim 9, wherein the IC chip further comprises a power terminal coupled to a gate-driver supply terminal having a voltage that is derived from the boosted output voltage.

11. The electronic device of claim 10, wherein the IC chip further comprises:
    a carbon monoxide detection circuit;
    a photo-detection circuit;

an ion detection circuit, each of the carbon monoxide detection circuit, the photo-detection circuit and the ion detection circuit being powered by the gate-driver supply terminal;

a horn driver; and a multiplexor coupled to the carbon monoxide detection circuit, the photo-detection circuit and the ion detection circuit.

12. The electronic device of claim 11, wherein the electronic device further comprises a smoke detector, the smoke detector including:

a carbon monoxide sensor;

a photo sensor;

an ion sensor;

a horn; and a microcontroller.

13. A method of operating a DC/DC boost converter, the method comprising:

receiving a target peak value for a peak inductor current; and dynamically changing the value of the peak inductor current responsive to one or more of a boosted output voltage and a switching frequency of the DC/DC boost converter;

determining a respective idle-state time for a respective switching cycle of the boost convertor;

decreasing the peak inductor current in response to a first number of consecutive respective switching cycles having a respective idle-state time greater than a first idle-state threshold; and decreasing the peak inductor current in response to a respective idle-state time greater than a second idle-state threshold.

14. The method of claim 13, wherein dynamically changing the value of the peak inductor current comprises:

setting the peak inductor current to an initial peak value at startup, the initial peak value being lower than the target peak value; and setting the peak inductor current to the target peak value in response to the boosted output voltage being greater than a threshold output voltage.

15. The method of claim 14, further comprising setting the peak inductor current to the initial peak value in response to the boosted output voltage dropping below the threshold output voltage, and setting the peak inductor current to the target peak value in response to the boosted output voltage being at least equal to the threshold output voltage.

16. The method of claim 13, wherein determining the duration of the respective idle-state time comprises:

setting, at a zero-current comparator, a zero current signal high in response to a switch-node voltage being equal to a first percentage of the boosted output voltage;

setting, at a boost-high comparator, a boosted-voltage-high signal high in response to the boosted output voltage being greater than a target output voltage; and counting clock cycles in response to a rising edge of the zero current signal and the boosted-voltage-high signal being high, the counting ceasing in response to a falling edge of the boosted-voltage-high signal.

17. The method of claim 13, further comprising:

monitoring the boosted output voltage; and increasing the peak inductor current in response to the boosted output voltage falling by a threshold amount.

* * * * *